(12) United States Patent
Govari

(10) Patent No.: US 8,401,624 B2
(45) Date of Patent: Mar. 19, 2013

(54) ECG SIGNAL ANALYSIS TOOL

(75) Inventor: Assaf Govari, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 386 days.

(21) Appl. No.: 12/327,267

(22) Filed: Dec. 3, 2008

(65) Prior Publication Data

US 2010/0137728 A1 Jun. 3, 2010

(51) Int. Cl.
*A61B 5/04* (2006.01)
*A61B 5/02* (2006.01)

(52) U.S. Cl. ......... 600/509; 600/508; 600/515; 600/517

(58) Field of Classification Search .......... 600/508–509, 600/515, 517
See application file for complete search history.

(56) References Cited

U.S. PATENT DOCUMENTS

| | | | |
|---|---|---|---|
| 4,742,458 A | 5/1988 | Nathans | |
| 4,884,345 A | 12/1989 | Long | |
| 5,109,862 A | 5/1992 | Kelen et al. | |
| 5,769,793 A | 6/1998 | Pincus et al. | |
| 5,868,680 A | 2/1999 | Steiner et al. | |
| 5,947,909 A | 9/1999 | Watrous | |
| 6,091,990 A | 7/2000 | Hsu et al. | |
| 6,178,261 B1 | 1/2001 | Williams | |
| 6,304,773 B1 | 10/2001 | Taylor et al. | |
| 6,615,075 B2 | 9/2003 | Mlynash et al. | |
| 6,684,100 B1 * | 1/2004 | Sweeney et al. | 600/517 |
| 6,983,183 B2 | 1/2006 | Thiagarajan et al. | |
| 2003/0059116 A1 | 3/2003 | Kupeev et al. | |
| 2005/0010124 A1 | 1/2005 | Couderc et al. | |
| 2005/0222513 A1 * | 10/2005 | Hadley et al. | 600/515 |
| 2007/0142737 A1 * | 6/2007 | Cazares et al. | 600/515 |

FOREIGN PATENT DOCUMENTS

EP 0489209 A1 6/1992

OTHER PUBLICATIONS

Goletsis, Y et al. Automated Ischemic Beat Classification Using Genetic Algorithms and Multicriteria Decision Analysis. IEEE Transactions on Biomedical Engineering, Oct. 2004 (51:10) 1717-1725.
F. Wang et al., "Learning Structural Knowledge from the ECG", Lecture Notes in Computer Science, Springer, DE, vol. 2199, Jan. 2001, pp. 288, 290 and 291.
A. Koski et al., "Syntactic recognition of ECG signals by attributed finite automata", Pattern Recognition, Elsevier, GB LNKD, vol. 28, No. 12, Dec. 1995, pp. 1927-1940.

* cited by examiner

*Primary Examiner* — Nicole F Lavert
(74) *Attorney, Agent, or Firm* — Louis J. Capezzuto

(57) ABSTRACT

A computer-implemented method for analyzing a physiological signal includes selecting a first time interval containing a pattern of interest in a recording of the physiological signal. Respective values of a characteristic of the physiological signal are computed in a plurality of time segments within the first time interval. The computed values are concatenated to form a signature of the pattern of interest. A further occurrence of the pattern of interest is identified in the physiological signal during a second time interval by matching the signal in the second time interval to the signature.

23 Claims, 3 Drawing Sheets

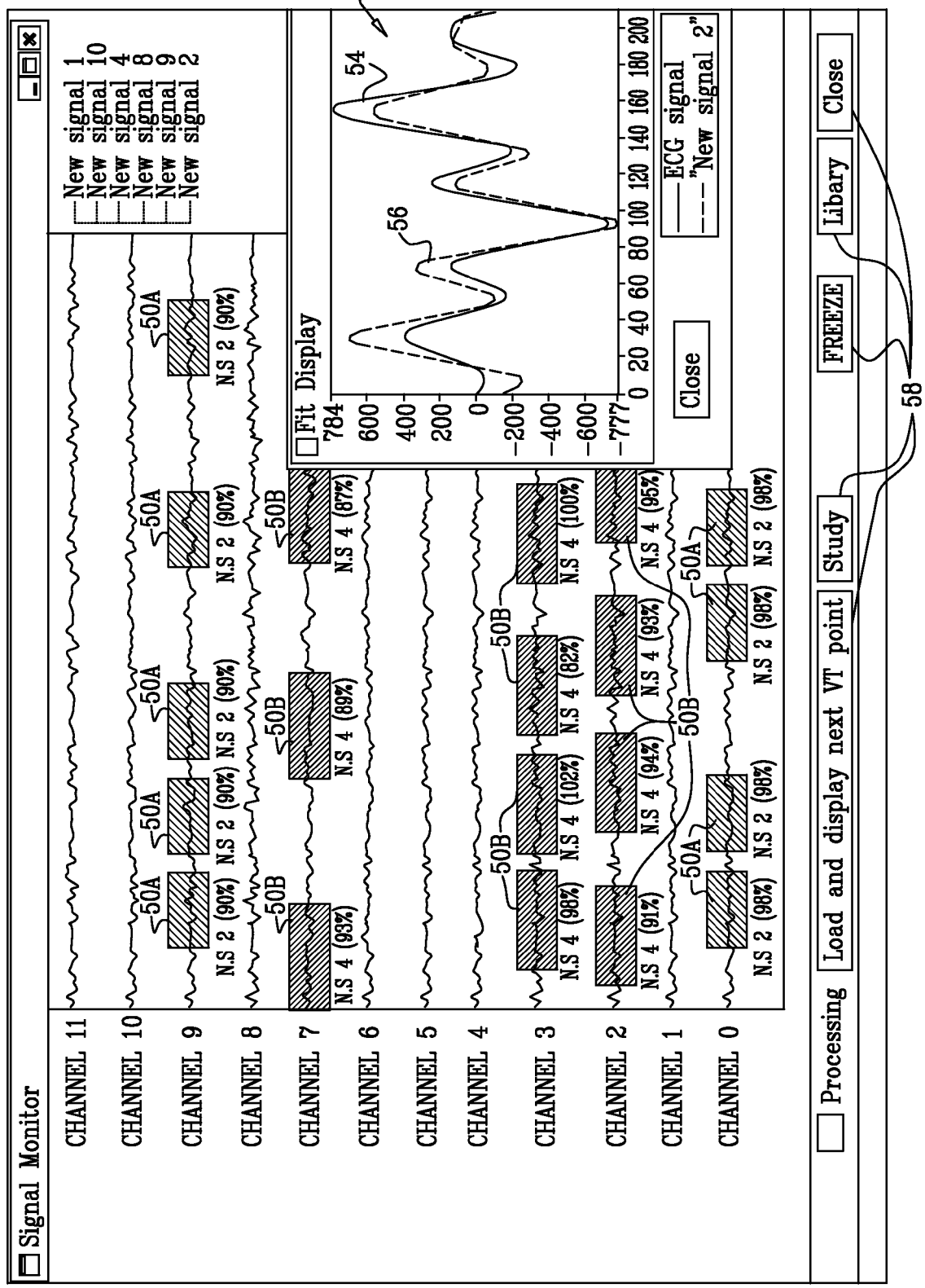

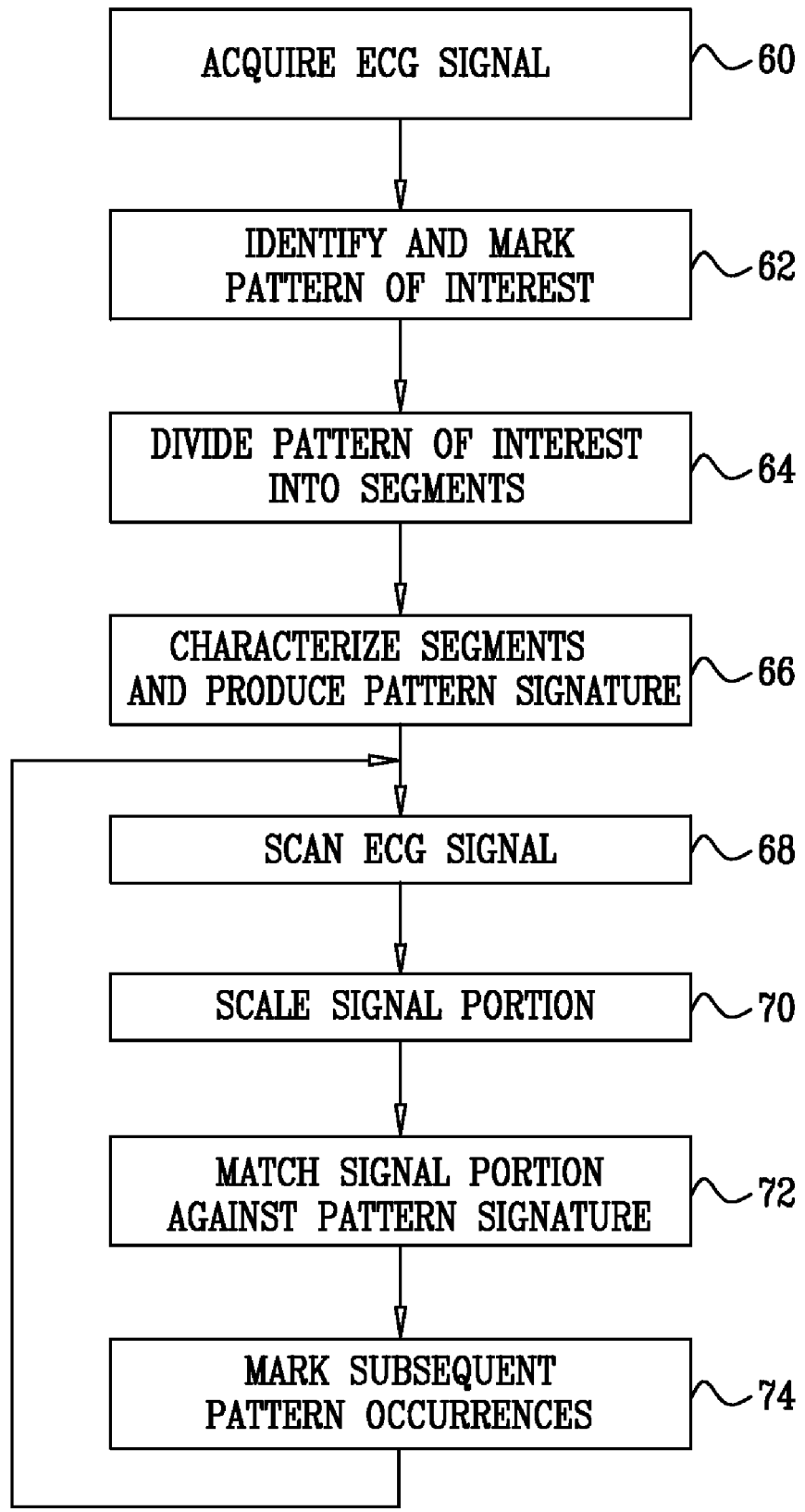

ECG SIGNAL ANALYSIS TOOL

FIELD OF THE INVENTION

The present invention relates generally to medical systems, and particularly to methods and systems for detecting patterns in physiological signals.

BACKGROUND OF THE INVENTION

Various methods and systems for analyzing electrocardiogram (ECG) signals are known in the art. For example, U.S. Pat. No. 6,091,990, whose disclosure is incorporated herein by reference, describes a method for plotting symbols representing complexes of selected arrhythmic events on an interactive display screen, for organizing, displaying and interacting with a patient's recorded arrhythmia episodes. A stored arrhythmic episode is selected from a plurality of arrhythmic episodes. A similarity value and a dissimilarity value are calculated for each complex of a plurality of complexes of the selected arrhythmic episode with respect to normal sinus rhythm complexes. Symbols representing the arrhythmic complexes are then plotted as a function of the calculated similarity and dissimilarity values on an interactive display screen.

As another example, U.S. Pat. No. 6,684,100, whose disclosure is incorporated herein by reference, describes a method for curvature-based complex identification and classification. The method includes sensing a cardiac signal and computing curvatures at sample points on the sensed cardiac signal. Features are then extracted from the computed curvatures, and the extracted features are compared with a set of predetermined templates. The sensed cardiac signal is classified based on the outcome of the comparison.

U.S. Pat. No. 5,109,862, whose disclosure is incorporated herein by reference, describes a frequency-domain signal processing and analysis method for ECG signals. Fourier analysis is applied to short overlapping segments of an ECG signal to create a three-dimensional map whose axes are time, frequency and power, thus disclosing changes in the frequency content of the ECG signal over short intervals of time.

U.S. Pat. No. 6,304,773, whose disclosure is incorporated herein by reference, describes a medical device, such as a defibrillator, which automatically detects and reports cardiac asystole. The device obtains ECG data and calculates one or more ECG measures based on the ECG data. The ECG data is classified into classes indicative of cardiac conditions, wherein one class is indicative of cardiac asystole. The defibrillator may classify the ECG data into a rhythm class associated with a cardiac rhythm, such as asystole, and report the rhythm class of the ECG data on the display. Statistical binary classification and regression trees may be used to classify the ECG data according to cardiac rhythm. Other signal data, such as impedance or phonocardiographic signal data may also be obtained and classified with the ECG data.

Other methods for classifying ECG signals are described, for example, by Goletsis et al., in "Automated Ischemic Beat Classification Using Genetic Algorithms and Multicriteria Decision Analysis," IEEE Transactions on Biomedical Engineering, (51:10), October, 2004, pages 1717-1725, which is incorporated herein by reference.

SUMMARY OF THE INVENTION

An embodiment of the present invention provides a computer-implemented method for analyzing a physiological signal, including:

selecting a first time interval containing a pattern of interest in a recording of the physiological signal;

computing respective values of a characteristic of the physiological signal in a plurality of time segments within the first time interval;

concatenating the computed values to form a signature of the pattern of interest; and identifying a further occurrence of the pattern of interest in the physiological signal during a second time interval by matching the signal in the second time interval to the signature.

In some embodiments, the physiological signal includes an electrocardiogram. Computing the values of the characteristic may include determining respective increase/decrease flags indicating one of an increase and a decrease of the physiological signal in each of the time segments.

In a disclosed embodiment, computing the values of the characteristic includes representing the values using respective characters, and concatenating the values to form the signature includes augmenting the characters to form a string. In an embodiment, matching the signal in the second time interval to the signature includes representing the signal in the second time interval using a character sequence and finding an occurrence of the string in the character sequence. In another embodiment, computing the values of the characteristic includes representing the values using respective bit values, and concatenating the values to form the signature includes augmenting the bit values to form a binary word.

In another embodiment, computing the values of the characteristic includes calculating a scaling parameter of the signal in the first time interval, and matching the signal in the second time interval to the signature includes scaling the signal in the second time interval responsively to the scaling parameter to match the signal in the first time interval. The scaling parameter may include a mean amplitude of the signal in the first time interval. In yet another embodiment, calculating the scaling parameter includes identifying a first dominant frequency in a first spectrum of the signal in the first time interval, and scaling the signal in the second time interval includes identifying a second dominant frequency in a second spectrum of the signal in the second time interval and scaling the second spectrum so that the second dominant frequency matches the first dominant frequency.

In some embodiments, identifying the further occurrence includes displaying the physiological signal to an operator, and marking the further occurrence on the displayed signal. In an embodiment, identifying the further occurrence comprises identifying multiple occurrences of the pattern of interest, and calculating and providing statistical information of the multiple occurrences to an operator.

In a disclosed embodiment, selecting the first time interval includes selecting multiple first intervals containing multiple respective instances of the pattern of interest, computing the values of the characteristic includes computing multiple sets of the values in parallel time segments within the respective first intervals, and concatenating the computed values includes computing the signature responsively to the multiple sets of the values.

There is additionally provided, in accordance with an embodiment of the present invention, apparatus for analyzing a physiological signal, including:

an input device, which is arranged to accept a selection of a first time interval containing a pattern of interest in a recording of the physiological signal; and a processor, which is arranged to compute respective values of a characteristic of the physiological signal in a plurality of time segments within the first time interval, to concatenate the computed values to form a signature of the pattern of interest, and to identify a further occurrence of the pattern of interest in the physiological signal during a second time interval by matching the signal in the second time interval to the signature.

There is also provided, in accordance with an embodiment of the present invention, a computer software product for analyzing a physiological signal, the product including a computer-readable medium, in which program instructions are stored, which instructions, when read by a computer, cause the computer to accept a selection of a first time interval containing a pattern of interest in a recording of the physiological signal, to compute respective values of a characteristic of the physiological signal in a plurality of time segments within the first time interval, to concatenate the computed values to form a signature of the pattern of interest, and to identify a further occurrence of the pattern of interest in the physiological signal during a second time interval by matching the signal in the second time interval to the signature.

The present invention will be more fully understood from the following detailed description of the embodiments thereof, taken together with the drawings in which:

BRIEF DESCRIPTION OF THE DRAWINGS

FIG. 2 is a diagram that schematically illustrates an exemplary display of an ECG signal analysis system, in accordance with an embodiment of the present invention; and FIG. 3 is a flow chart that schematically illustrates a method for analyzing ECG signals, in accordance with an embodiment of the present invention.

DETAILED DESCRIPTION OF THE INVENTION

Figure 1:
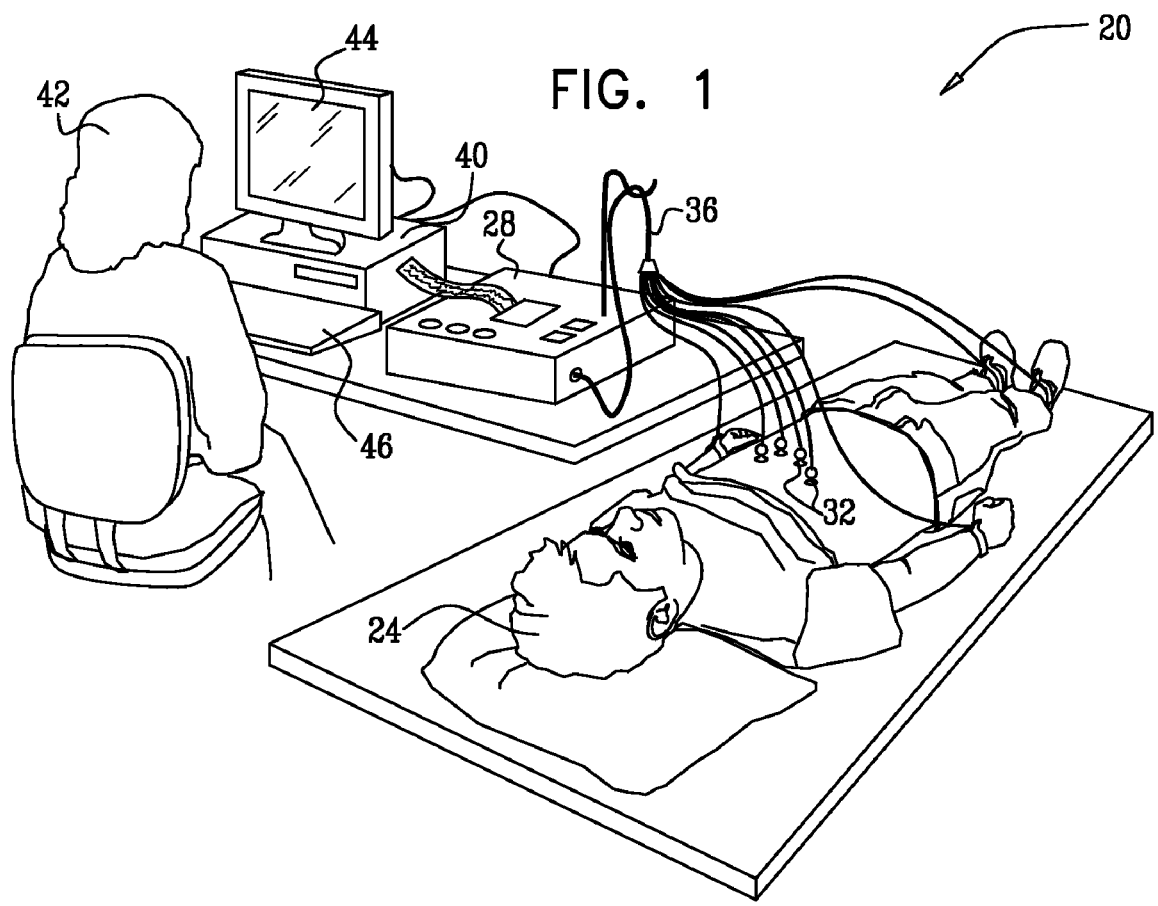
FIG. 1 is a schematic pictorial illustration of an ECG signal analysis system, in accordance with an embodiment of the present invention.

Embodiments of the present invention provide improved methods and systems for automatically detecting patterns of interest in ECG and other physiological signals. Such patterns are often indicative of certain medical conditions and events. Successful detection of these patterns may have significant diagnostic value.

In some embodiments, an ECG analysis system performs ECG measurements on a patient and displays the measured ECG signals to a physician. The physician identifies an exemplary occurrence of a pattern of interest in the displayed signals and indicates the time interval containing the pattern to the system.

A pattern processor analyzes the time interval and produces a characteristic signature of the pattern. Typically, the processor divides the time interval into multiple segments along the time axis and calculates a signal characteristic in each of the segments. The processor uses the sequence of signal characteristics of the different segments as the pattern signature. For example, the signal characteristic may comprise an indication whether the signal increases or decreases in the segment.

The pattern processor scans the ECG signal and detects other occurrences of the pattern of interest. The processor identifies time intervals, in which the signal matches the pattern signature. In some embodiments, the pattern signature comprises a string, in which the signal characteristic value of each segment is represented by a corresponding character. In these embodiments, the processor detects occurrences of the pattern using a string matching process. The detected pattern occurrences are marked and displayed to the physician.

The methods and systems described herein relieve the physician of the tedious and time-consuming task of manually scanning lengthy ECG signal traces to detect a pattern of interest. Moreover, these methods and systems are based on automatic analysis of an exemplary pattern and not on an explicit quantitative definition of the pattern, which is sometimes difficult to specify.

FIG. 1 is a schematic, pictorial illustration of an ECG signal analysis system 20, in accordance with an embodiment of the present invention. The system measures the ECG of a patient 24 using an ECG monitor 28. The ECG monitor uses one or more electrodes 32 attached to the patient's body. The electrodes sense the electrical activity of the patient's heart and produce corresponding electrical signals, referred to herein as ECG signals. The ECG signals are provided to the ECG monitor via a cable 36. The ECG monitor typically outputs ECG traces that plot the ECG signals as a function of time.

An operator 42, typically a cardiologist or other physician, examines the ECG signals and attempts to identify cardiac conditions, such as cardiac events or pathologies, which are of interest. In many cases, cardiac conditions are indicated by characteristic patterns in the ECG signals. The operator is often able to detect isolated occurrences of a particular pattern of interest in the ECG signals. Manually detecting multiple occurrences of such patterns in a lengthy set of ECG traces, however, is an extremely tedious, time-consuming and error-prone task. On the other hand, specifying the pattern of interest quantitatively and explicitly in order to enable automatic detection with sufficient quality is often difficult. Experienced cardiologists are frequently able to identify segments of the ECG signal that appear to have diagnostic importance, as transient indicators of abnormality, for example, without necessarily being able to quantify the reasons for such an identification.

The methods and systems described herein automatically detect occurrences of a pattern of interest, based on an example of the pattern that is identified by the operator. In some embodiments, the ECG signals measured by monitor 28 are provided to a pattern processor 40. The pattern processor displays the ECG signals to the operator using a display 44. An exemplary display screenshot is described in FIG. 2 below. The operator identifies and marks one or more patterns of interest in the displayed signals using an input device 46, such as a keyboard or a mouse. Processor 40 learns the characteristics of the marked patterns and automatically identifies other occurrences of the patterns in subsequent and/or previously-recorded ECG signals.

In principle, the operator marks or otherwise indicates to processor 40 a time interval that contains the pattern of interest. Processor 40 divides the marked interval into multiple segments along the time axis, and characterizes the behavior of the ECG signal in each of the segments. In a typical implementation, the interval is divided into between five and ten segments. Alternatively, however, any other suitable number of segments can be used.

The sequence of signal characteristic values in the different segments of the time interval is used by processor 40 as a pattern signature. The processor then scans the ECG signals in order to find other occurrences of the pattern, i.e., other time intervals in which the ECG signal matches the signature. The pattern characterization and matching process is described in greater detail in FIG. 3 below.

Typically, processor 40 comprises a general-purpose computer, which is programmed in software to carry out the functions described herein. The software may be downloaded to the processor in electronic form, over a network, for example, or it may alternatively be supplied to the processor on tangible media, such as CD-ROM. Further alternatively, some elements of processor 40 may be implemented using hardware or using a combination of hardware and software elements.

The configuration of system 20 is an exemplary configuration, chosen purely for the sake of conceptual clarity. The methods described herein can also be used in alternative system configurations. For example, the functionality of ECG monitor 28 and pattern processor 40 can be integrated into a single unit. Such a unit may be implemented in a small, portable ECG analysis unit worn by the patient over a long period of time. Alternatively, rather than analyzing ECG measurements in real time, processor 40 may be used in an off-line manner to find patterns in a previously-acquired set of ECG measurements. In some embodiments, processor 40 can also provide statistical information regarding the pattern occurrences, such as the total number of occurrences within a certain time period and the average rate of occurrences.

Additionally or alternatively, the pattern of interest may be provided externally, such as from a library of characteristic ECG patterns. System 20 can also be used to define a library of patterns that have been found to be associated with certain types of pathologies or events. This library may be distributed to other cardiologists or systems for use in processing ECG signals gathered from other patients.

FIG. 2 is a diagram that schematically illustrates an exemplary screenshot display of system 20, as displayed to the physician on display 44, in accordance with an embodiment of the present invention. The figure shows twelve ECG signals originating from twelve electrodes 32. Two patterns of interest, denoted "new signal 2" and "new signal 4," have been previously defined by the physician. Processor 40 simultaneously detects occurrences of the two patterns in the ECG signals. In the present example, the detected occurrences are marked using shaded areas on the displayed ECG signals. Alternatively, the occurrences can be marked using any other suitable indication, such as using different color, icons or highlighted areas.

Occurrences of the "new signal 2" pattern are denoted 50A and marked with a certain shading pattern, while occurrences of the "new signal 4" pattern are denoted 50B and marked with a different pattern. The quality or confidence level of the match is indicated as a percentage next to each occurrence.

A fitting window 52 shows the matching of a particular occurrence to the pattern of interest. Curves 54 and 56 respectively show the pattern and one of the occurrences, laid one on top of the other. Various controls 58 enable the physician to freeze the displayed ECG signals, select a particular occurrence, add another pattern of interest, etc. The screenshot shown in FIG. 2 is an exemplary display. In alternative embodiments, any other suitable man-machine interface (MMI) features and methods can be used.

FIG. 3 is a flow chart that schematically illustrates a method for analyzing ECG signals, in accordance with an embodiment of the present invention. The method begins with system 20 acquiring an ECG signal, at an acquisition step 60. The acquired signal is displayed to the operator, either in real time or off-line. The operator identifies and marks a time interval that contains a pattern of interest, at a pattern indication step 62.

Pattern processor 40 divides the time interval marked by the operator into multiple segments, at a segmentation step 64. The pattern processor characterizes the ECG signal in each of the segments and produces a pattern signature based on the sequence of signal characteristics, at a signature generation step 66. For example, the processor may determine, for each segment, whether the signal increases or decreases along the segment. The processor can then generate a sequence of "ascending" and "descending" indications, which is used as a characteristic signature of the pattern of interest. In these embodiments, the number of segments is typically selected with sufficient resolution, so that the signal inside each segment is likely to be monotonous.

Additionally or alternatively, the processor can use any other suitable parameter in order to characterize the different segments, such as the positive or negative slope of the signal within the segment, the signal amplitude, normalized amplitude, DC offset, frequency spectrum and/or signal fragmentation.

In some embodiments, processor 40 represents the pattern signature as a string, in which each segment is represented by a character. For example, a segment in which the signal increases can be represented by a "U" character. A segment in which the signal decreases can be represented by a "D" character. The characters representing the segments are then concatenated to form a string such as "UDDUUDUDU . . . UUD", which is used as a signature. The signature can also be represented using a binary word in which each bit indicates whether the signal increases or decreases in the respective segment (e.g., "0" indicates a decreasing segment and "1" indicates an increasing segment, or vice versa.)

In some embodiments, processor 40 measures one or more scaling parameters of the ECG signal in the marked time interval. These scaling parameters are stored together with the signature and are later used for matching other occurrences of the pattern. For example, the mean amplitude of the signal can be used as a scaling parameter. Additionally or alternatively, the processor may calculate a spectrum of the pattern of interest and determine one or more dominant frequencies in the spectrum. The dominant frequencies can be used as scaling parameters.

Having generated the pattern signature, processor 40 scans the ECG signal and attempts to detect other occurrences of the pattern of interest, at a scanning step 68. Depending on the system configuration used, processor 40 may monitor real time or buffered ECG measurements as they are acquired, or scan in an off-line manner through a body of previously-measured ECG signals.

The processor scales a portion of the scanned ECG signal responsively to the scaling parameters of the pattern of interest, at a scaling step 70. For example, the processor may normalize the mean amplitude of the scanned signal to match the mean amplitude of the pattern of interest. As another example, the processor may perform spectral scaling of the scanned signal, so that its dominant frequencies match the dominant frequencies of the pattern of interest. Spectral scaling can be viewed as scaling (i.e., stretching or compressing) the time axis of the scanned signal with respect to the time axis of the pattern of interest. The processor may compute a fast Fourier transform (FFT) of the scanned signal portion for this purpose.

Processor 40 attempts to find intervals in the scanned ECG signal that match the pattern signature, at a matching step 72. For example, when the pattern of interest is represented using a string, the processor divides the scanned and scaled signal portion into segments, characterizes each segment and assigns a character to each segment. The scanned signal portion is thus represented by a long string of characters. Then, the processor attempts to find the sub-string that represents the pattern signature in the string that represents the scanned signal portion. Any suitable string matching process known in the art can be used for this purpose. Each match is considered to be an occurrence of the pattern in the scanned signal.

Processor 40 marks the detected occurrences on display 44, at an occurrence indication step 74. Typically, the processor marks the time intervals that are detected as pattern occurrences. Since the processor may search for several patterns simultaneously, the pattern being detected is indicated next to each occurrence. In some embodiments, each occurrence is also given a unique name or number that is displayed. The processor may also display a confidence level or a quality metric of the match next to each detected occurrence.

In some embodiments, the operator identifies and marks multiple examples (instances) of a given pattern of interest to processor 40, and the processor calculates the pattern signature based on the multiple examples. This feature often improves the matching performance, for example when measurement noise is high, or when one or more of the examples has a poor quality or is not sufficiently representative of the sought pattern. Typically, processor 40 divides the different examples into the same number of segments and combines the signal characteristics in parallel segments (i.e., corresponding segments in the different pattern examples). The processor may combine the signal characteristics from the parallel segments by averaging, filtering, weighting, majority voting, or any other suitable combining technique.

Although the embodiments described herein mainly address identifying patterns in an ECG signal, the principles of the present invention can also be used for detecting patterns in other physiological signals, such as electroencephalogram (EEG) and respiratory signals.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A computer-implemented method for analyzing a physiological signal, comprising:
   selecting a first time interval containing a pattern of interest in a recording of the physiological signal;
   computing respective values of a characteristic of the physiological signal using respective characters in a plurality of time segments within the first time interval such that each segment is represented by a character, wherein each character represents an increase in the physiological signal or a decrease in the physiological signal for each segment in the plurality of time segments;
   concatenating the computed values to form a signature of the pattern of interest by augmenting the characters to form a string; and
   identifying a further occurrence of the pattern of interest in the physiological signal during a second time interval by matching the signal in the second time interval to the signature.

2. The method according to claim 1, wherein the physiological signal comprises an electrocardiogram.

3. The method according to claim 1, wherein computing the values of the characteristic comprises determining respective increase/decrease flags indicating one of an increase and a decrease of the physiological signal in each of the time segments.

4. The method according to claim 1, wherein matching the signal in the second time interval to the signature comprises representing the signal in the second time interval using a character sequence and finding an occurrence of the string in the character sequence.

5. The method according to claim 1, wherein computing the values of the characteristic comprises representing the values using respective bit values, and wherein concatenating the values to form the signature comprises augmenting the bit values to form a binary word.

6. The method according to claim 1, wherein computing the values of the characteristic comprises calculating a scaling parameter of the signal in the first time interval, and wherein matching the signal in the second time interval to the signature comprises scaling the signal in the second time interval responsively to the scaling parameter to match the signal in the first time interval.

7. The method according to claim 6, wherein the scaling parameter comprises a mean amplitude of the signal in the first time interval.

8. The method according to claim 6, wherein calculating the scaling parameter comprises identifying a first dominant frequency in a first spectrum of the signal in the first time interval, and wherein scaling the signal in the second time interval comprises identifying a second dominant frequency in a second spectrum of the signal in the second time interval and scaling the second spectrum so that the second dominant frequency matches the first dominant frequency.

9. The method according to claim 1, wherein identifying the further occurrence comprises displaying the physiological signal to an operator, and marking the further occurrence on the displayed signal.

10. The method according to claim 1, wherein identifying the further occurrence comprises identifying multiple occurrences of the pattern of interest, and calculating and providing statistical information of the multiple occurrences to an operator.

11. The method according to claim 1, wherein selecting the first time interval comprises selecting multiple first intervals containing multiple respective instances of the pattern of interest, wherein computing the values of the characteristic comprises computing multiple sets of the values in parallel time segments within the respective first intervals, and wherein concatenating the computed values comprises computing the signature responsively to the multiple sets of the values.

12. Apparatus for analyzing a physiological signal, comprising:
   an input device, which is arranged to accept a selection of a first time interval containing a pattern of interest in a recording of the physiological signal; and
   a processor, which is arranged to compute respective values of a characteristic of the physiological signal in a plurality of time segments within the first time interval by representing the values of the characteristic using respective characters such that each segment is represented by a character, wherein each character represents an increase in the physiological signal or a decrease in the physiological signal for each segment in the plurality of time segments, and to concatenate the computed values to form a signature of the pattern of interest by augmenting the characters to form a string, and to identify a further occurrence of the pattern of interest in the physiological signal during a second time interval by matching the signal in the second time interval to the signature.

13. The apparatus according to claim 12, wherein the physiological signal comprises an electrocardiogram.

14. The apparatus according to claim 12, wherein the processor is arranged to determine respective increase/decrease flags indicating one of an increase and a decrease of the physiological signal in each of the time segments.

15. The apparatus according to claim 12, wherein the processor is arranged to represent the signal in the second time interval using a character sequence, and to find an occurrence of the string in the character sequence so as to match the signal in the second time interval to the signature.

16. The apparatus according to claim 12, wherein the processor is arranged to represent the values of the characteristic using respective bit values, and to form the signature by augmenting the bit values to form a binary word.

17. The apparatus according to claim 12, wherein the processor is arranged to calculate a scaling parameter of the signal in the first time interval, and to scale the signal in the second time interval responsively to the scaling parameter when matching the signal in the second time interval to the signature.

18. The apparatus according to claim 17, wherein the scaling parameter comprises a mean amplitude of the signal in the first time interval.

19. The apparatus according to claim 17, wherein the processor is arranged to identify a first dominant frequency in a first spectrum of the signal in the first time interval, to identify a second dominant frequency in a second spectrum of the signal in the second time interval, and to scale the second spectrum so that the second dominant frequency matches the first dominant frequency.

20. The apparatus according to claim 12, wherein the processor is arranged to display the physiological signal to an operator and to mark the further occurrence on the displayed signal.

21. The apparatus according to claim 12, wherein the processor is arranged to identify multiple occurrences of the pattern of interest, and to calculate and provide statistical information of the multiple occurrences to an operator.

22. The apparatus according to claim 12, wherein the input device is arranged to accept the selection of multiple first intervals containing multiple respective instances of the pattern of interest, and wherein the processor is arranged to compute multiple sets of the values in parallel time segments within the respective first intervals, and to compute the signature responsively to the multiple sets of the values.

23. A computer software product for analyzing a physiological signal, the product comprising a computer-readable non-transitory medium, in which program instructions are stored, which instructions, when read by a computer, cause the computer to accept a selection of a first time interval containing a pattern of interest in a recording of the physiological signal, to compute respective values of a characteristic of the physiological signal in a plurality of time segments within the first time interval using respective characters such that each segment is represented by a character, wherein each character represents an increase in the physiological signal or a decrease in the physiological signal for each segment in the plurality of time segments, to concatenate the computed values to form a signature of the pattern of interest by augmenting the characters to form a string, and to identify a further occurrence of the pattern of interest in the physiological signal during a second time interval by matching the signal in the second time interval to the signature.

* * * * *